United States Patent [19]

Abe et al.

[11] Patent Number: 5,110,949

[45] Date of Patent: May 5, 1992

[54] METHOD OF SYNTHESIZING LEUKOTRIENE B$_4$ AND DERIVATIVES THEREOF

[75] Inventors: Yoshihiro Abe, Tokyo, Japan; Kyriacos C. Nicolaou, Havertown, Pa.

[73] Assignee: University of Pennsylvania, Philadelphia, Pa.

[21] Appl. No.: 388,990

[22] Filed: Sep. 13, 1989

Related U.S. Application Data

[62] Division of Ser. No. 165,521, Mar. 8, 1988, Pat. No. 4,873,024.

[51] Int. Cl.$^5$ ............................................ C07D 309/12
[52] U.S. Cl. .................................. 549/214; 549/415; 549/416; 549/420; 549/423
[58] Field of Search ...................... 549/214, 416, 423; 560/254, 263, 264

[56] References Cited

PUBLICATIONS

Just et al., Can. J. Chem., 1983, 61 (4), 712–717.
Just et al., Tetrahedron Letters, 1982, 23 (22), 2285–8.
Williams et al., JACS, 1984, 106, 2641–2644.
Nicolaon et al., JCS, Chem. Comm., 1982, (22), 1292–3.
Nicolaon et al., Angew. Chem., 1987, 99 (10), 1077–9 (C.A., 107:236,269y, 1987).
Corey, E. J., Marfat, A., Goto, G., Brion, F., J. Am. Chem. Soc., 102, 7986 (1980).
Corey, E. J., Marfat, A., Munroe, J., Kim, K. S., Hopkins, P. B., Brion, F., Tetrahedron Lett., 22, 1077 (1981).
Guindon, Y., Zamboni, R., Lau, C.-K., Rokach, J., Tetrahedron Lett., 23, 739–742, (1981).
Zamboni, R., Rokah, J., Tetrahedron Lett., 23, 2631–2634 (1982).
Mills, L. S., North, P. C., Tetrahedron Lett., 24, 409 (1983).
Nicolaou, K. C., et al., "A General and Stereocontrolled Total Synthesis of Leukotriene B$_4$ and Analogues," J. Am. Chem. Soc., 106, 3748–3551 (1984).

Primary Examiner—Nicky Chan
Attorney, Agent, or Firm—Woodcock Washburn Kurtz Mackiewicz & Norris

[57] ABSTRACT

An improved method for synthesizing leukotriene B$_4$ and derivatives thereof is disclosed, as are novel intermediates used in the process. Unlike prior art processes, the method of this invention involves a step in which 2(R)-[[(1,1-dimethylethyl)diphenylsilyl]oxy]dec-4 (Z)-ene-1-ol or a related compound is coupled with methyl-[5(S)-[[1,1dimethylethyl)-diphenylsilyl]oxy]-dec-8 (E)-10-(dimethylphosphono)-6-ynoate.

1 Claim, 2 Drawing Sheets

METHOD OF SYNTHESIZING LEUKOTRIENE B4 AND DERIVATIVES THEREOF

This is a division of application Ser. No. 165,521, filed Mar. 8, 1988 now U.S. Pat. No. 4,873,024.

BACKGROUND OF THE INVENTION

1. Field of the Invention

This invention relates to a novel and improved method for synthesizing leukotriene B4 and derivatives thereof, and to novel intermediates useful in said process.

2. The Prior Art

Leukotriene B4 (hereinafter "LTB4", illustrated as Compound 1 in FIG. 1) is an important metabolite of the 5-lipoxygenase arachidonic acid peroxidation pathway recently isolated by incubation with polymorphonuclear leukocytes. Borgeat, P; Samuelsson, B., *J. Biol. Chem.*, 254, 2643 (1979). Implicated as a mediator in inflammation, this biomolecule exhibits potent chemotactic properties, facilitates adhesion of neutrophils to the endothelium, causes degranulation and release of lysosomal enzymes, increases the intracellular levels of calcium ions, and induces vascular permeability. Smith, M. J. H., *Gen. Pharmacol.*, 12, 211 (1981); Ford Hutchinson, A. W., *J. R. Soc. Med.*, 75, 831 (1981); Borgeat, P., Sirois, P., *J. Med. Chem.*, 24, 121 (1981); Samuelsson, B., *Science (Washington, D.C.)*, 220, 568 1983); Piper, P. J., *Trends Pharmacol. Sci.*, 1983, 4, 75. The major use for LBT4 is as a research tool for stimulating certain physical states. For example, it can be used for stimulating inflammation for testing antiinflammatory compounds.

Due to its physiological importance and its low natural abundance, several syntheses of LTB4 have already appeared. Corey, E. J., Marfat, A., Goto, G., Brion, F., *J. Am Chem. Soc.*, 102, 7984 (1980); Corey, E. J., Marfat, A., Munroe, J., Kim, K. S., Hopkins, P. B., Brion, F., *Tetrahedron Lett.*, 22, 1077 (1981); Guindon, Y., Zamboni, R., Lau, C.-K., Rokach, J., *Tetrahedron Lett.*, 23, 739, 2631 (1982); Mills, L. S., North., P. C., *Tetrahedron Lett.*, 24, 409 1983). One of the more successful synthesis methods known in the art is that disclosed in Nicolau, K. C., Zipkin, R. D., Dolle, R. E. and Harris, B. D., "A General and Stereocontrolled Total Synthesis of Leukotriene B4 and Analogues," *J. Am. Chem. Soc.*, 106, 3548 (1984). This process is illustrated in the chemical flow chart shown in FIG. 2. Aldehyde 9 is coupled with the anion of phosphonate 6 to afford product 10. Pure 10, obtained after chromatographic separation, is then subjected to controlled hydrogenation (Lindlar catalyst, $CH_2Cl_2$) to afford a mixture of tetraene 8, monoacetylene 11, and recovered starting material. Finally, removal of all three protecting groups from 8 with excess $n\text{-}Bu_4NF$ leads to LTB4 1. While this process represents an improvement over many of the previously known processes for preparing LTB4, there is still a need for a process which will provide LTB4 in fewer steps and greater yields.

It is therefore an object of this invention to provide a process which can be used to prepare LTB4 and useful analogues thereof. It is another object of this invention to provide novel intermediate compounds which can be used in the preparation of LTB4 and useful analogues thereof.

SUMMARY OF THE INVENTION

A novel process has now been found for preparing LTB4 and analogues thereof which process represents an improvement over previously known processes in terms of both yield and ease of preparation. The process comprises the following steps:

(a) hydrogenating a compound of the formula

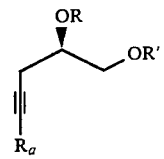

where R and R' are different from one another and are protecting groups, and $R_a$ is a hydrocarbon group, to reduce the acetylene bond;

(b) removing the protecting group R' at position 1 from the product of step (a);

(c) oxidizing the product of step (b) to convert the alcohol group at position 1 to an aldehyde;

(d) coupling the product of step (c) with a compound of the formula

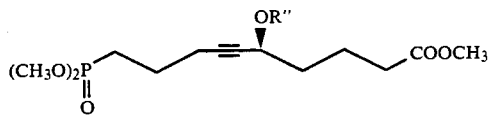

where R" is a protecting group;

(e) hydrogenating the product of step (d) to reduce the acetylene bond;

(f) removing the protecting groups R and R" from the product of step (e) to yield a compound of the formula

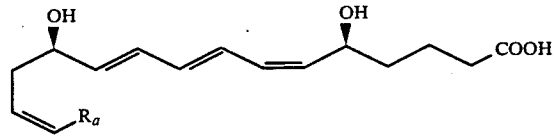

A number of the intermediate compounds in this process are novel and are considered part of this invention. This invention therefore also relates to novel compounds of the formulas:

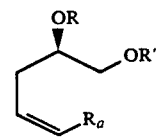

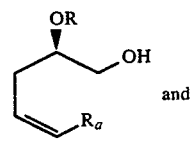

and

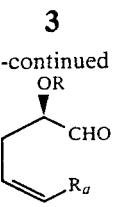

where R, R', R" and $R_a$ are as defined above.

Protecting groups R, R' and R" are selected from groups well know in the art useful for protecting oxygen atoms from oxidation. Examples of suitable protecting groups include but are not limited to those which react with the oxygen to form esters, such as acetate or t-butyl carbonyl, groups which react with the oxygen to form ethers, such as Sit-Bu(phenyl)$_2$ and Sit-Bu(methyl)$_2$, and groups such as tetrahydropyran (THP) and

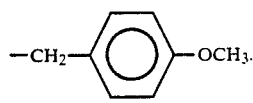

In the preferred embodiment, R=R"=Sit-Bu(phenyl)$_2$ and R'=THP.

The hydrocarbon moieties from which $R_a$ is selected can include $C_1$-$C_6$ linear alkyl groups, optionally substituted at their terminis with a benzyl group, a phenyl group, or a $C_1$-$C_2$ haloalkyl group; $C_3$-$C_6$ cycloalkyl groups; $R_b$=O where $R_b$ is a $C_1$-$C_5$ alkyl group. The benzyl and phenyl groups may optionally be substituted with substituents known in the art. Preferably, $R_a$ is selected from the group consisting of n-pentyl, cyclohexyl, —(CH$_2$)$_4$—$R_c$ where $R_c$ is selected from CF$_3$, cyclohexyl, benzyl and phenyl. More preferably, $R_a$ is selected from n-pentyl and —(CH$_2$)$_4$—CF$_3$.

Preferred novel intermediate compounds of this invention have the formulas:

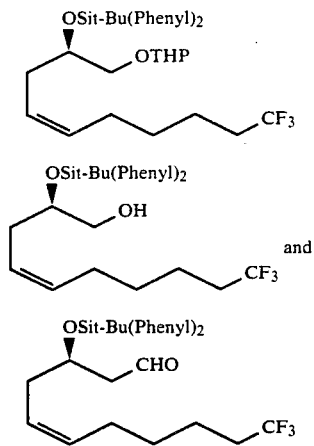

DETAILED DESCRIPTION OF THE INVENTION

Figure 1:
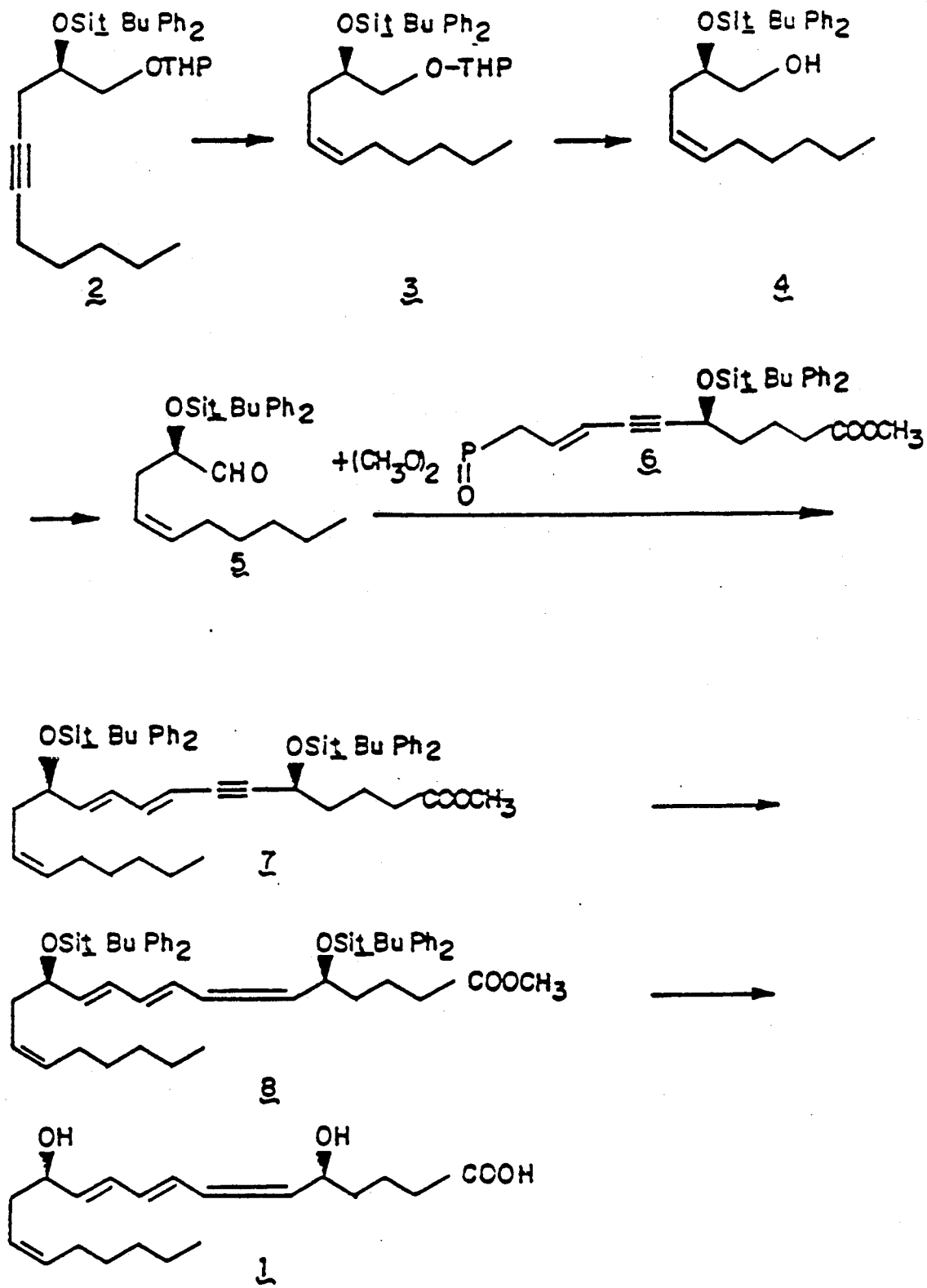
FIG. 1 is a schematic representation of a process of this for preparing LTB4.

The process of this invention is described in more detail below in terms of a specific embodiment of the invention, namely, the process for preparing LTB4. This process is schematically represented in FIG. 1. Although the following description is limited in scope to the preparation of LTB4 alone, the process of this invention is also useful for preparing numerous analogues of LTB4.

The chemical formulas of many of the compounds mentioned in the discussion to follow are presented in the schematic representation of the method of this invention in FIG. 1. For the sake of simplifying this disclosure, the compounds will be referred to by the numerical label given them in FIG. 1. The chemical names for such compounds are as follows:

1 - leukotriene B$_4$
2 - 1-[(tetrahydro-2H-pyran-2-yl)oxy]2(R)-[[1,1-dimethylethyl)diphenylsilyl]oxy]-dec-4-yne
3 - 1-[(tetrahydro-2H-pyran-2-yl)oxy]-2(R)[[1,1-dimethylethyl)diphenylsilyl]oxy]-dec-4(z)-ene
4- 2(R)-[[(1,1-dimethylethyl)diphenylsilyl]oxy]dec-4(z)-en-1-ol
5- 2(R)-[[(1,1-dimethylethyl)diphenylsilyl]oxy]-dec-4(z)-en-1-al
6- methyl-[5(S)-[[(1,1-dimethylethyl)diphenylsilyl]oxy]-dec-8(E)-ene-10-(dimethylphosphono)-6-ynoate]
7- methyl-[5(S), 12(R)-bis[[(1,1-dimethylethyl)diphenylsilyl]oxy]-8(E), 10(E), 14(z)-eicosatrien-6-ynoate
8- methyl-[5(S), 12(R)-bis[[(1,1-dimethylethyl)diphenylsilyl]oxy]-6(Z), 8(E), 10(E), 14(Z)-eicosatetraenoate The starting material for the process of this invention, compound 2, can be prepared as described in Nicolaou, K. C. et al., "A General and Stereocontrolled Total Synthesis of Leukotriene B$_4$ and Analogues," J. Am. Chem. Soc., 106, 3548 (1984) or Hanson, R. M. and Sharpless, K. B., J. Org. Chem., 51 1922 (1986). Briefly, optically active (S)-glycidol THP ether is prepared from ascorbic acid as disclosed in Takano, S., Numata, H., Ogasawara, K., Heterocycles, 19, 237 (1982) and Baldwin, J. J., Raab, A. W., Mensler, K., Arison, B. H., McClure, D. E., J. Org. Chem., 43, 4876 (1978). The ether is reacted (−78−25° C.) with two equivalents of the anion of 1-heptyne (1.0 equiv. of n-BuLi, 1.0 equiv. of TMEDA and THF, −78° C.) to afford a-[(tetrahydro-2H-pyran-2-yl)oxy] dec-4-yn-2(R)-ol which is then silylated (t-BuPh$_2$SiCl, imidazole, DMF) to , compound 2.

In the first step of the process of this invention, compound 2 is hydrogenated to reduce the acetylene bond between carbon atoms 4 and 5. This can be accomplished by contacting compound 2, in a suitable inert solvent, with an effective amount of a hydrogenation catalyst under a hydrogen atmosphere for a period of time effective to reduce substantially all acetylene bonds. Suitable catalysts include Lindlar catalysts. Generally, the hydrogenation may be carried out under ambient conditions for a period of about two to three hours. Compound 3 may be isolated by filtration of the reaction mixture, and removal of solvent followed by flash column chromatography.

In the next step of the process of this invention, protecting group R' at position 1 is removed by, for example, contacting a solution of compound 3 with a protonic acid (or Lewis acid) such as pyridinium p-toluene sulfonate. This mixture is preferably maintained at a constant temperature within the range of about 20° to 50° C. for a period of about fifteen to twenty-four hours. Compound 4 may be isolated by concentrating the reaction mixture, diluting it with ether and water, followed by separation, washing of the organic layer, drying and flash column chromatography.

The next step of the process of the invention entails oxidizing compound 4 to yield the corresponding aldehyde 5. This can be done by methods known in the art for oxidizing alcohols to aldehydes, e.g., by the method disclosed in Mancuso, A. J., Huang, S.-L., Swern, D., *J. Org. Chem.*, 43, 2480 (1978).

In the process of this invention, the aldehyde 5 is next coupled with phosphonate 6 to yield compound 7. The coupling of aldehyde 5 and phosphonate 6 is preferably carried out by combining solutions of each component in the presence of a strong base (e.g., lithium bis-trimethylsilylamide, lithium diisopropylamide, or sodium hydride) at a temperature within the range of about $-78°$ C. to $20°$ C. for a period of about one-half to three hours. Suitable solvents include benzene or ethers such as tetrahydrofuran.

Product 7 is converted to LTB4 (Compound 1) by first subjecting the compound to hydrogenation conditions similar to those discussed above in connection with step (a) to reduce the acetylene bond and produce compound 8. The alcohol-protecting groups on compound 8 are removed by methods known in the art, e.g, by reacting with n-Bu$_4$NF under an argon atmosphere. Nicolaou, K. C., et al., *J. Am. Chem. Soc.*, supra.

Figure 2:
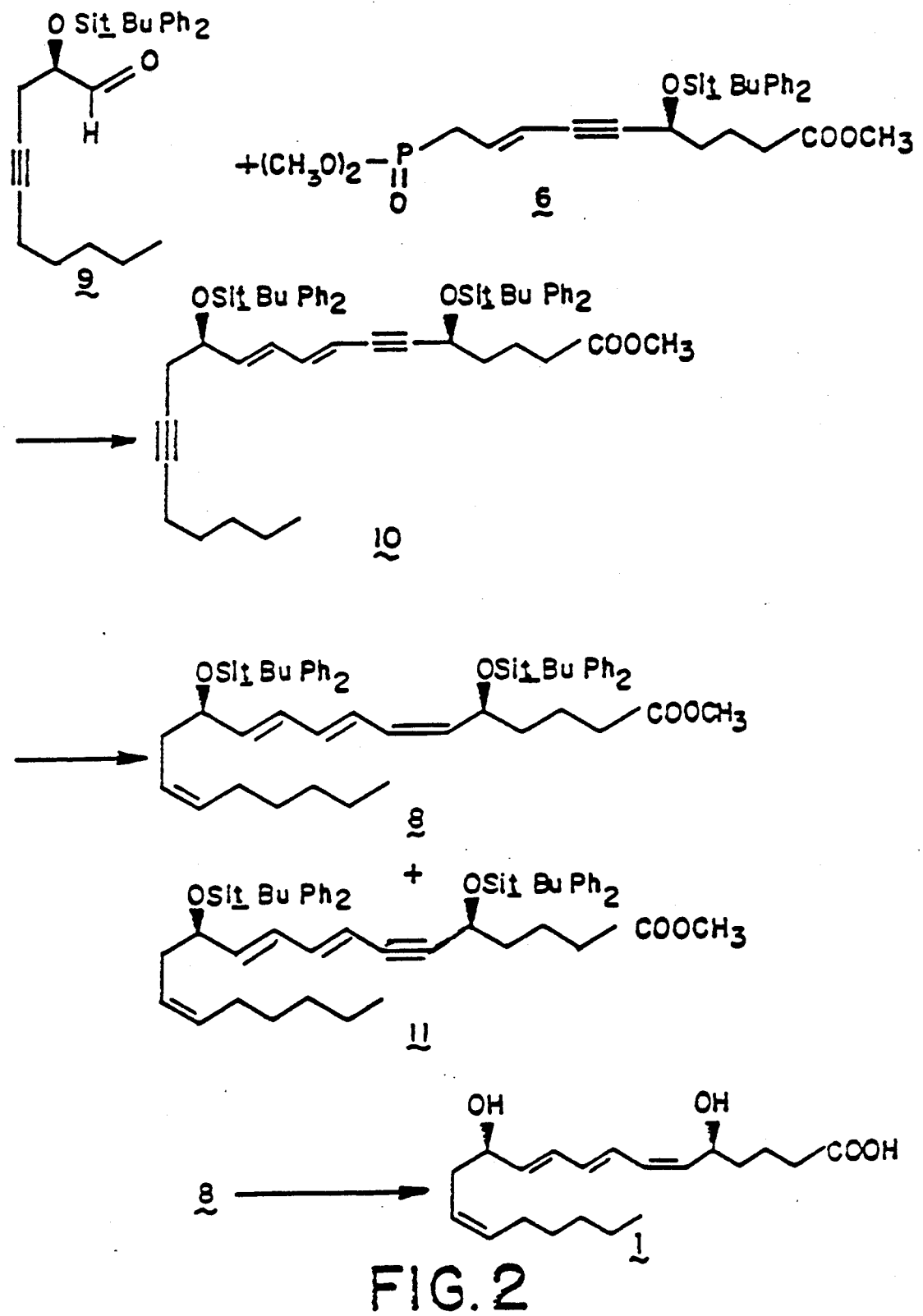
FIG. 2 is a schematic representation of a prior art process for preparing LTB4.

In comparing the process of this invention with the prior art process schematically represented in FIG. 2, it can be seen that the major difference between these two processes is that, while the prior art process entails the coupling of two acetylene compounds (9 and 6), in the process of this invention, the acetylene bond of starting material 2 is reduced prior to any further syntheses steps. The advantage of the process of this invention over the prior art process is that it produces product in greater yields and which can be more easily purified.

The process of this invention and the preparation of the novel intermediate compounds of this invention is further illustrated in the following examples.

EXAMPLE 1

Synthesis of Leukotriene B4 a. Preparation of (S) Glycidol-tetrahydropyran ether (S)-Glycidol (2 g, 27.0 mmol) in dihydropyran (40 mL, 438.0 mmol) was treated with para-toluenesulphonic acid (0.3 g, 1.5 mmol) at $0°$ C. with magnetic stirring. The reaction was complete in 10 minutes (TLC, ether). The reaction mixture was diluted with ether (100 mL), washed with water (10 mL), saturated NaHCO$_3$ solution (20 mL), brine (20 mL) and dried over MgSO$_4$. Concentration and flash chromatography gave the title compound (3 g, 70%).

Liquid; b.p. $110°$ C. (20 mm); R$_f$=0.39 (50% ether in petroleum ether); $[\alpha]^{25}{}_D$-12.09 (C=0.062, CH$_2$Cl$_2$); IR (neat):2920 (s),2860 (m), 1450 (m), 1380 (m), 1350 (m), 1255 (m), 1200 (m), 1120 (s), 1060 (s), 1030 (s), 960 (m), 890 (m) cm$^{-1}$; $^1_H$ NMR (250 MHz, CDCl$_3$) δ: 4.66 (m, 1H, OCHO), 3.84–4.01 (m, 4H, CH$_2$O), 3.20 (m, 1H epoxide), 2.84 (dt, J-2.0, 5.0 H$_z$, 1H, epoxide), 2.60 and 2.70 (dd, J=7.0, 2.5 Hz, ½ H each epoxide), 1.90–1.46 (m, 6H, CH$_2$), CI mass spec., m/e (rel. intensity)L 158.0 (M+, 0.7) 157.0 (M+-1, 7.8), 117.0 (11.2), 101.0 (23.3), 85.0 (base peak); HRMS calcd. for C$_8$H$_{14}$O$_3$: 158.0943, found: 158.0906.

b. Preparation of 1-[(Tetrahydro-2H-pyran-2-yl)oxy]-deca-2(R)-ol-4-yne

To the magnetically stirred solution of 1-heptyne (2.79 g, 29.0 mmol) and tetramethylethlenediamine (3.36 g, 29.0 mmol) in THF (8 mL) under argon was added a 1.6M solution of n-butyllithuim (18.1 mL, 29.0 mmol) at $-78°$ C. the reaction mixture was warmed to $-20°$ and stirred at that temperature for 15 minutes. The reaction mixture was cooled again to $-78°$ C. and treated dropwise with a solution of (S)-glycidol-THP (2.29 g, 14.5 mmol) in THF (3 mL). the reaction mixture was slowly warmed to $25°$ C. and stirred at that temperature for 16H, then quenched with a mixture of ice (100 g) and ether (150 mL). The organic phase was washed with 1M CuSO$_4$ aq. solution (2×50 mL), water (25 mL), brine (50 mL), and dried (MgSO$_4$). Removal of the solvents followed by flash column chromatography (30% ether in petroleum ether) afforded the title compound (3.0 g) in 81% yield.

Oil; R$_f$=0.12 (30% ether in petroleum ether); $[\alpha]^{25}{}_D$-12.57 (C=0.028), CHCl$_3$); IR (neat): 3440 (m), 2940 (s), 2880 (s), 1456 (m), 1440 (m), 1382 (m), 1354 (m), 1325 (m), 1262 (m), 1202 (m), 1184 (m), 1130 (s), 1124 (s), 1075 (s), 1062 (s), 1032 (s), 972 (m), 908 (m), 870 (m), 810 (m), cm$^{-1}$; $^1$H NMR (250 MHz, CDCl$_3$) δ: 4.61 (bs, 1H, OCHO), 4.00–3.49 (m, 5H, CH$_2$O, CHOH, CH$_2$CHO), 3.29 (d, 0.5H, CH$_2$OH, J=4.0 Hz), 2.99 (d, 0.5H, CH$_2$OH, J=5.0 Hz), 2.50–2.37 (m, 2H, H-3), 2.16 (bt, 2H,H-6, J=7.0 Hz), 1.93–1.70 (m, 2H, CH$_2$), 1.68–1.44 (m, 6H,CH$_2$), 1.42–1.25 (m, 4H, CH$_2$), 0.91 (t, 3H, H-10, J=6.2 Hz); mass spec., m/e (rel. intensity): 254.1 (0.2, M+), 237.1 (0.6), 219.1 (0.3), 197.0 (1.0), 183.1 (10.2), 145.0 (12.3), 140.0 (1.6), 109.1 (3.3), 85.0 (base peak); HRMS: calculated for C$_{15}$H$_{26}$O$_3$: 254.1882, found: 254.1866.

c. Preparation of Compound 2

To a magnetically stirred solution of the product of step (b) in DMF (12 mL) under argon was added imidazole (2.4 g, 35.4 mmol) followed by dropwise addition of t-butyldiphenylsilyl chloride. The reaction mixture was stirred overnight or until no starting material remained (TLC). The reaction was quenched with ice water (50 mL), diluted with ether (200 mL), washed with water (2×50 mL), brine (50 mL), and dried (M$_g$SO$_4$). Removal of the solvents and purification by flash chromatography (2% to 5% ether in petroleum ether) provided compound 2 (5.6 g) in 95% yield.

57: Oil R$_f$=0.20 (5% ether in petroleum ether); $[\alpha]^{25}{}_D$-12.48 (c-0.23, CHCl$_3$); IR (neat): 3075 (m), 3050 (m), 2935 (s), 2860(s), 1958 (w), 1890, (w), 1820 (w), 1590 (w), 1460 (m), 1428(m), 1110 (s), 820 (m), 742 (m), 705 (s) cm$^{-1}$; $^1$H NMR (250 mHz, CDCl$_3$) δ:7.84–7.68 (m, 4H, aromatic), 7.48–7.29 (m, 6H, aromatic), 4.59–4.45 (m, 1H OCHO), 4.05–3.93 (m,1H, CHO), 3.84–3.69 (m,2H, CH$_2$O), 3.50–3.34 (m, 2H CH$_2$O), 2.44–2.23 (m,2H, H-3), 2.08 (bt, 2H, H-6, J-7.0 Hz), 1.84–1.22 (m,12H, CH$_2$), 1.06 (s, 9H, $^t$Bu , 0.88 (t,3H, H-10, J=6.2 Hz); mass spec., m/e (rel. intensity): 492.2 (0.2, M+), 436.2 (01.), 409.2 (o.4), 351.1 (16.0). 331.2 (10.5), 241.1 (25.5), 221.0 (10.0), 199.0 (17.1) 85.0 (base peak); HRMS: calculated for C$_{31}$H$_{44}$O$_3$Si: 492.3060, found: 492.2975.

d. Preparation of Compound 3

To a n-hexane solution of 2 (500 mg, 1.02 mmol in 100 ml), 50 mg of lindlar catalyst (Filuka, 10 wt %) was added and stirred for 2.5 hours under a hydrogen atmosphere (balloon). Filtration over celite and removal of the solvent followed by flash column chromatography (5% ether in petroleum ether) provided 3 (489.5 mg; 97.4%).

3: oil, Rf=0.19 (5% ether in petroleum ether, developed twice); $[\alpha]^{21}_D$ −12.46 (C=0.0126, CHCl$_3$); IR (neat) 3085(m) 3060(m) 2945(s), 2865(s), 1435(m), 1118(s), 1062(s), 827(m), 745(m), 707(s) cm$^{-1}$; $^1$H-NMR (250 MHz, CDCl$_3$)δ: 7.72–7.65 (m,4H, aromatic), 7.43–7.30 (m,6H, aromatic), 5.40–5.30 (m,2H olefinic), 4.52–4.43 and 4.40–4.35 (m,1H, H-2'), 3.94–3.78 (m,1H, H-2), 3.75–3.5 (m,2H), 3.42–3.35 (m,1H) and 3.30–3.20 (m,1H, —CH$_2$O—), 2.25–2.14 (m,2H, H-3), 1.87–1.70 (m,2H, H-6), 1.68–1.10 (m,12H), 1.03 (s) and 1.04 (S,9H, tBu), 0.86 (t,J=6.7 Hz) and 0.85 (t,J=6.7 Hz, H-10); HRMS: Calc'd. for (M+1) C$_{31}$H$_{47}$O$_3$Si: 495.3294, found: 495.3257.

e. Preparation of Compound 4

To a stirring solution of 3 (3.6 g, 7.3 mmol) in 150 ml of methanol, 91 mg (0.05 eq.) of pyridinium p-toluene sulfonate (PPTS) was added. The mixture was stirred at constant temperature (40° C.) in an oil bath for 22 hours. After concentration to a volume of c.a. 30 ml under reduced pressure and dilution with ether (200 ml) and water (50 ml), organic layer was separated and aqueous layer was extracted once again with ether (100 ml). Combined organic layers were washed with saturated sodium bicarbonate solution, brine, and dried over magnesium sulfate. Removal of the solvents and flash column chromatography (10% ether in petroleum ether) provided 4 (2.76 g) in 92.4% yield. 4: oil; Rf=0.24 (10% ether in petroleum ether); $[\alpha]^{21}_D$ −33.47 (C=0.0147, CHCl$_3$); IR (neat) 3600 (broad), 3470 (broad), 3082 (m), 3060(m), 2965(s), 2940(s), 2870(s), 1435(s), 1115(broad, s), 828(m), 735(s), 705(s) cm$^{-1}$; $^1$H-NMR (250 MHz, CDCl$_3$)δ: 7.7–7.64 (m, 4H, aromatic), 7.43–7.32 (m, 6H, aromatic), 5.38–5.25 (m, 1H, olefinic), 5.20–5.10(m, 1H, olefinic), 3.80–3.73(m,1H,H-2), 3.60–3.35 (m,2H,H-1), 2.40–2.10(m,2H,H-3), 1.85–1.73 (m,3H,H-6,OH), 1.06 (s,9H,$^t$Bu), 1.34–1.05(m,6H), 0.84 (t,J=6.5 Hz, 3H,H-10). HRMS: Calc'd. for (M-OH) C$_{26}$H$_{37}$OSi: 393.2614, found: 393.2644.

f. Preparation of Compound 5

In a round-bottomed flask with a septum, oxalyl chloride (0.795 ml, 1.5 eq) and methylene chloride (22.4 ml) were placed and cooled to −78° C. under an argon atmosphere. After dropwise addition of dimethylsulfoxide (0.86 ml, 2eq), the mixture was stirred for 30 minutes at −78° C. A solution of 4 (2.5 g, 6.07 mmol) in 8 ml of methylene chloride was added dropwise and stirred for 30 minutes. Then, 4.22 ml of triethylamine (5 eq) was added and stirred at −78° C. for 30 minutes and for an additional half hour upon warming up to room temperature. The reaction mixture was diluted with ether (200 ml) and washed twice with water, and three times with brine. Drying over magnesium sulfate and removal of the solvent provided produced yellow oil (2.58 g). After flash chromatography (7% ether in petroleum ether), 2.38 g of 5 was obtained (95.7%).

5: colorless oil; Rf=0.34 (5% ether in petroleum ether); $[\alpha]^{21}_D$ −16.42 (C=0.0134, CHCl$_3$); IR (neat) 3082 (m), 3062 (m), 3022 (w), 2970(s), 2865 (s), 1750 (s), 1435 (s), 1117 (s), 829 (m), 738 (m), 708 (s) cm$^{-1}$; $^1$H-NMR (250 MHz, CDCl$_3$)δ: 9.54(d,J=1.7 Hz, 1H, H-1), 7.67–7.61 (m,4H, aromatic), 7.47–7.31 (m,6H, aromatic), 5.50–5.29 (m,2H, H-4, H-5), 4.04(dt, 1H,J=6 Hz, 1.7 Hz, H-2), 2.55–2.25 (m,2H, H-3), 1.95–1.80 (m,2H, H-6), 1.40–1.15 (m,6H), 1.10 (s,9H, $^t$Bu), 0.85 (t, 3H, J=6.5 Hz, H-10); HRMS: Calc'd for C$_{26}$H$_{37}$O$_2$Si: 409.2563, found: 409.2565.

g. Preparation of Compound 7

Phosphonate 6 (383 mg, 0.71 mmol) was dissolved in THF (5 ml) and cooled to −78° C. under argon atmosphere. Lithium bistrimethylsilylamide (1.0 M THF solution, 0.68 ml, 0.68 mmol) was added dropwise with stirring. After 30 minutes, THF solution of aldehyde 5 (240 mg, 0.59 mmol in 1.2 ml of THF) was introduced and stirred at −78° C. for 3 hours. The reaction mixture was warmed to room temperature with stirring for 10 minutes, then poured into a mixture of sat. ammonium chloride solution (25 ml) and ether (100 ml). Aqueous layer was extracted with ether, and the combined organic layers were washed with water, twice with brine, and dried over magnesium sulfate. Removal of the solvent under reduced pressure and flash column chromatography provided 7 (382 mg) in 78.8% yield.

7: oil; R$_f$=0.08 (2% ethyl acetate in petroleum ether); $[\alpha]^{25}_D$ −46.98 (C=0.145, CHCl$_3$); IR (neat): 3070 (m), 3040(m), 3010 (m), 2920 (s), 2850(s), 1734 (s), 1582 (W), 1424 (m), 1166 (m), 1100 (s), 958 (m), 810 (m), 726 (m), 690 (s) cm$^{-1}$, $^1$H NMR (250 MHz, CDCl$_3$)δ: 7.78–7.60 (m, 8H, aromatic), 7.50–7.28 (m,12H, aromatic), 6.17 (dd, 1H, H-9, J=15.4, 10,6 Hz), 5.88 (dd, 1H, H-10, J-15.2, 10.9 Hz), 5.66 (dd, 1H, H-11, J=6.2, 15.0 Hz), 5.46–5.18 (m,3H, H8, 14,15), 4.57 (bt, 1H, H-5), 4.18 (m, 1H, H-12), 3.65 (s,3H, COOCH$_3$), 2.35–2.14 (m,4H, H-2, 13), 1.89–1.65 (m,6H), 1.35–1.14, (m,6H), 1.08 (s, 18H, $^t$Bu), 0.87 (t,3H, H-20, J=6.2 Hz); CI Mass spec. m/e (rel. intensity): 824.9 (M+, 0.2), 771.0 (5.1), 712.9 (4.2), 568.0 (0.5), 513.0 (1.2), 460.9 (1.1), 369.0 (2.2), 311.0 (2.9), 258.9 (3.1), 198.9 (base peak); HRMS: Calc'd. for C$_{53}$H$_{68}$O$_4$Si$_2$: 824.4656, found: 824.4676.

h. Preparation of Compound 8

To a n-hexane solution of 7 (1.0 g, 1.2 mmol in 100 ml), 100 mg of Lindlar catalyst (Fluka, 10 wt %) was added and stirred for one hour under a hydrogen atmosphere (balloon). An additional 50 mg of catalyst was added and stirred until 7 was consumed (28 hours) monitored by TLC (2% ethyl acetate-petroleum ether). Catalyst was removed by filtration over celite, and the filtrate was concentrated under reduced pressure. Flash column chromatography gave 952 mg of 8 (95.0%)

8: oil; R$_f$=0.11 (2% ethyl acetate in petroleum ether); $[\alpha]^{25}_D$ +32.96 (c=0.016, CH$_2$Cl$_2$); IR (neat): 3070 (m), 3010 (m), 2920 (s), 2850 (s), 1734 (s), 1582 (w), 1420 (m), 1100 (s), 810 (m), 726 (m), 690 (s) cm$^{-1}$; $^1$H NMR (250 MHz, CDCl$_3$)δ: 7.74–7.58 (m, 8H aromatic), 7.44–7.25 (m,12H aromatic), 5.93 (dd, 1H, H-10, J=15/1, 10.5 Hz), 5.87–5.56 (m,4H), 5.46–5.17 (m,3H), 4.54–4.42 (m,1H, H-5), 4.23–4.12 (m, 1H, H-12), 3.61 (s,3H, COOCH3), 2.30–2.08 (m,4H), 1.87–1.77 (m, 2H), 1.62–1.37 (m,4H), 1.32–1.12 (m,6H), 1.10 (s, 9H, $^t$Bu , 1.05 (s, 9H, $^t$Bu), 0.85 (t, 3H, H-20, J=6.2 Hz): CI mass spec., m/e (rel. intensity): 826.9 (M+, 0.5), 770.9 (3.3), 715.0 (8.5), 636.7 (0.4), 571.0 (1.3), 515.0 (1.5), 459.0 (3.2), 360.9 (0.7), 318.9 (3.4), 295.0(4.1), 238.9 (6.2), 198.9 (base peak); HRMS: Calc'd. for C$_{53}$H$_{70}$O$_4$Si$_2$, found: 826.4813.

i. Preparation of LTB4

To a magnetically stirred solution of 8 (52 mg, 0.06 mmol) in THF (2.0 ml) at room temperature was added nBu$_4$NF (1M, THF, 0.60 ml, 0.60 mmol) under argon atmosphere. The reaction mixture was stirred for 5 hours (TLC monitoring) and diluted with ether (50 mL) and brine (2mL). The aqueous layer was exhaustively extracted with ether (5×30 mL) and dried (M$_g$SO$_4$). Concentration and purification by flash chromatography gradient elution: 100% ether to 50% methanol in ether) provided by LTB$_4$ (16 mg, 73%). RP-HPLC (Altex ultrasphere, ODS 5u, 4.6 mm×25 cm column; CH$_3$OH:H$_2$O:AcOH:conc. NH$_4$OH, 67:33:0.08:0.07 mobile phase) showed greater that 95% purity.

LTB$_4$: oil; R$_f$=0.22 (2% methanol in ether); IR (neat) 3360 (s), 3020 (w), 2970 (m), 2935 (s), 2960 (m), 1715 (s) cm$^{-1}$; $^1$H NMR (250 MHz, CDCl$_3$) δ:6.47 (dd, 1H,H-8, J=14.0, 12.0 Hz), 1.28 (m,2H, H-9, H-10), 6.09 (t,1H, H-7, J=11.0 Hz), 5.78 (dd, 1H, H-11, J=15.0, 6.5 Hz), 5.65-5.25 (m, 4H, H-6, H-14, H-15, OH), 4.62 (m,1H, H-5), 423 (m,1H, H-12), 2.35 (m, 4H, CH$_2$), 2.04 (m,2H, CH$_2$), 1.80-1.15 (m, 12H, CH$_2$, OH), 0.90 (t, 3H, H-20, J=6.5 Hz); UV max (CH$_3$OH) 260, 270, 281 nm (e 38,000, 50,000, 39,000).

EXAMPLE 2

Synthesis of 20,20,20- Trifluoro LTB4 a. Preparation of:

10,10,10 - Trifluoro-1-[(tetrahydro-2H-pyran-2-yl) oxy]-deca-2(R)-ol-4-yne (Compound 12)

To the magnetically stirred solution of 7,7,7-trifluoro-1-heptyne (3 g. 20 mmol) and tetraethylethylenediamine (3 ml, 20 mmol) in THF 15 ml) under argon was added a 1.6M solution of n-butyllithium (12.5 ml, 20 mmol) at −78° C. The reaction mixture was stirred for 25 minutes. A solution of 2(S)-glycidol-THP (1.58 g, 10 mmol) in THF (5 ml) was added dropwise and the reaction mixture was stirred for 2 hours at −78° C., then it was warmed to 0° C. and stirred for 3 hours. The reaction mixture was warmed to room temperature and kept stirring for an additional 16 hours. It was quenched with a mixture of ice 50 g and ether 160 ml. The organic phase was washed with 1M CuSO4 aqueous solution (50 ml×3), water (25 ml), sat. NaHCO$_3$ (25 ml), water (25 ml), brine (50 ml), and dried (MgSO$_4$). Removal of the solvents followed by flash column chromatography (20% ether in petroleum ether) provided 12 (1.18 ) in 38.3% yield. (46.7% based on 17.9% recovery of glycidol)

12: oil; Rf=0.141 (30% ether in Petroleum ether); 1H-NMR (250 MHz, CDCl$_3$)δ: 4.6-4.5 (m, 1H, H-2' of THP), 4.0-3.4 (m, 5H, CH$_2$O, CHOH, CH$_2$CHO), 3.30 (d,0.5H, J=3.5 Hz,-OH), 2.99 (d,0.5H, J=5.2 Hz —OH), 2.5-2.2 (m,2H, 3-H), 2.2-1.9 (m,4H, H-6, H-9), 1.9-1.6 (m, 10H, CH$_2$); HRMS (CI) Calc'd. for (M+NH$_4$)$^+$: C$_{15}$H$_{27}$O$_3$NF$_3$ 326.1943, found: 326.1956.

b. Preparation of:

10,10,10-Trifluoro-1-[(Tetrahydro-2H-pyran-2-yl)oxy]-2-(R)-[[(1,1-dimethylethyl) diphenysilyl]oxy]-dec-4-yne (Compound 13)

To a magnetically stirred solution of 12 (830 mg, 2.69 mmol) in DMF (3 ml) under argon was added imidiazole (548 mg, 3eq) followed by dropwise addition of t-butyldiphenylsilyl chloride (0.92 ml). The reaction mixture was stirred over night, then it wa poured into a mixture of ether (100 ml) and water (50 ml). The aqueous phase was extracted with ether, and the combined organic layers were washed with water, brine, and dried over MgSO$_4$. Removal of the solvents and purification by flash column chromatography (2%-10% ether in petroleum ether) provided 13 (1.18 g) in 80.5% yield.

13: oil; Rf=0.33 (10% ether in petroleum ether); [α]$^{19}$$_D$=−8.42 (C=0.0105, CHCl$_3$); IR (neat) 3075 (w), 3050 (w), 2940 (s), 2860 (s), 1440 (m), 1258 (s), 1202 (s), 1114 (s), 1038 (s), 996 (m), 824 (m), 742 (m), 704 (s) cm$^{-1}$; 1H-NMR (250 MHz, CDCl$_3$) δ: 7.8-7.6 (m, 4H, aromatic), 7.45-7.3 (m, 6H, aromatic), 4.4-4.6 (m, 1H, H-2' of THP), 4.05-3.93 (m, 1H, H-2), 3.85-3.64 (m, 2H), 3.45-3.32 (m, 2H), 2.5-2.25 (m, 2H, H-3), 2.25-1.95 (m, 4H, H-6, H-9), 1.9-1.35 (m, 10H, —CH$_2$—), 1.062 (s) and 1.056 (s), (9H, $^t$Bu); HRMS Calc'd. for (M+NH$_4$)$^+$:C$_{31}$H$_{45}$O$_3$NF$_3$Si: 564.3121, found: 564.311.

c. Preparation of:

10,10,10-Trifluoro-1-[(tetrahydro-2H-pyran-2-yl)oxy]-2-(R)-[[1,1dimethylethyl)diphenylsilyl]oxy1-dec-4-ene (Compound 14)

To a n-hexane solution of 13 (1.18 g, 2.16 mmol, in 100 ml), 60 mg of Lindlar catalyst (Fluka, 5 wt %) was added and stirred for 17 hours under a hydrogen atmosphere (balloon). Additional 60 mg of catalyst was introduced and stirred for 8 hours. Filtration over celite and removal of the solvent followed by flash column chromatography (5% ether in petroleum ether) provided 14 (1.11 g; 94.5%).

14: oil; Rf=0.26 (5% ether in petroleum ether); [α]$^{19}$$_D$=−10.87 (C=0.0103, CHCl$_3$); IR (neat) 3070 (w), 3050 (w), 3015 (w), 2940 (s), 2860 (s), 1255 (s), 1110 (a), 1045 (s), 820 (m), 740 (m), 700 (s) cm$^{-1}$; $^1$H-NMR (250 MHz, CDCl$_3$) δ: 7.75-7.65 (m, 4H, aromatic), 7.45-7.3 (m, 6H, aromatic), 5.5-5.3 (m, 2H, olefinic, 4H, H-5), 4.55-4.4 (m, 1H, H-2' of THP), 4.02-3.86 (m, 1H, H-2), 3.8-3.55 (m, 2H),3.5-3.35 (m,1H), 3.35-3.24 (m, 1H), 2.3-2.15 (m, 2H), 2.15-1.85 (m, 4H), 1.85-1.2 (m, 10H, —CH$_2$—), 1.07 (s) and 1.06 (s) ($^t$Bu, 9H); HRMS Calc'd. for (M+NH$_4$)$^+$: C$_{31}$H$_{47}$O$_3$F$_3$Si: 566.328, found: 566.328.

d. Preparation of:

10,10,10 - Trifluoro-2(R)-[[(1,1-dimethylethyl)diphenylsilyl]oxy]-dec-4-en-1-ol (Compound 15)

To a stirring solution of 14 (1.11 g, 2.03 mmol) in 50 ml methanol, 30 mg of pyridinium p-toluene-sulfonate (PPTS) was added. The mixture was stirred at a constant temperature (40° C.) in an oil bath for 35 hours. After concentration to a column of c.a 10 ml under reduced pressure and dilution with ether (100 ml) and water (20 ml), the organic layer was separated and the aqueous layer was extracted with ether (50 ml). combined organic layers were washed with saturated sodium bicarbonate solution, brine, and dried over magnesium sulfate. Removal of the solvents and flash column chromatography (10% ether in petroleum ether) provided 15 (825 mg) in 87.8% yield. 15: oil; Rf=0.367(5% ether in petroleum ether); [α]$^{19}$$_D$=−31.17 (C=0.0103, CHCl$_3$); IR (neat) 3585 (m), 3460 (m, broad), 3070 (m), 3045 (w), 3018 (m), 2925 (s), 2885 (m), 2860 (s), 1255 (s), 1140 (s), 1110 (s), 1030 (m), 740 (m), 703 (s) cm$^{-1}$; $^1$H-NMR (250 MHz, CDCl$_3$) δ: 7.72-7.65 (m, 4H, aromatic , 7.47-7.34 (m, 6H, aromatic), 5.38-5.17 (m, 2H, olefin), 3.83-3.73 (m, 1H, H-2), 3.59-3.41 (m, 2H, H-1), 2.36-1.77 (m, 7H, H-3, H-6, H-9, —OH), 1.52-1.38 (m, 2H), 1.35-1.20 (m, 2H), 1.075 (s, 9H, $^t$Bu).

e. Preparation of:

10,10,10 - Trifluoro-2(R)-[[(1,1-dimethylethyl)diphenylsilyl]oxy]-dec-4(Z)-en-1-al (Compound 16)

In a round-bottomed flask with a septum, dimethyl sulfoxide (0.252 ml, 2.0 eq) and methylene chloride (8 ml) were placed and cooled to −78° C. under an argon atmosphere. After dropwise addition of oxalyl chloride (0.233 ml, 1.5 eq), the mixture was stirred for 30 minutes at −78° C. A solution of 15 (825 mg, 1.78 mmol) in 0.9 ml methylene chloride was added dropwise and stirred for 30 minutes. Then, 1.24 ml of triethylamine (5.0 eq) was added and stirred at −78° C. for 30 minutes and for an additional half hour upon warming up to room temperature. The reaction mixture was diluted with ether (200 ml) and washed twice with water, and three times with brine. Drying over magnesium sulfate, removal of the solvent and successive flash column chromatography (5% ether in petroleum ether) provided 16 (781.8 mg, 95.2%).

16: oil; Rf=0.463 (10% ether in petroleum ether); $[\alpha]^{19}{}_D = -12.73$ (C=0.0104, CHCl$_3$), IR (neat), 3065 (w), 3042 (w), 3010 (w), 2930 (s), 2890 (s), 2855 (s), 1738 (s), 1428 (m), 1254 (s), 1135 (s), 1110 (s), 700 (s) cm$^{-1}$; $^1$H-NMR (250 MHz, CDCl$_3$) δ9.57 (d, 1H, J=1.6 Hz, —CHO), 7.7-7.6 (m, 4H, aromatic), 7.5-7.3 (m, 6H, aromatic), 5.55-5.35 (m, 2H, olefinic), 4.06 (ddd, 1H, J=1.6 Hz, 6 Hz, 6 Hz, H-2), 2.5-2.25 (m, 2H, H-3), 2.15-1.85 (m, 4H, H-6, H-9), 1.6-1.25 (m, 4H, H-7, H-8), 1.11 (s, 9H, $^t$Bu); HRMS Calc'd. for $(M+H)^+$: $C_{26}H_{34}O_2F_3Si$ 463.2280, found: 463.2230.

f. Preparation of:
Methyl -20,20,20- trifluoro-5(S), 12 (R)-bis[[(1,1-dimethylethyl)-diphenylsilyl]oxy]-8(E), 10(E),14(Z)-eicosatriene-6-ynoate (Compound 17)

Phosphate 6 (132 mg, 0.24 mmol) was dissolved in THF (2 ml) and cooled to −78° C. under argon atmosphere. Lithium bis(trimethylsilyl)amide (1.0 THF solution, o.233 ml, 0.23 mmol) was added dropwise with stirring. After minutes, THF solution of aldehyde 16 (94 mg, 0.2 mmol, in 1 ml of THF) was introduced and stirred at −78° C. for 3 hours. The reaction mixture was warmed to room temperature with stirring for 10 minutes, then poured into a mixture of sat. ammonium chloride solution (20 ml) and ether and the combined organic layers were washed with water, twice with brine, and dried over magnesium sulfate. Removal of the solvent and flash column chromatography provided 17 (94.8 mg) in 53.0% yield.

17: oil; Rf=0.34 (10% ether in petroleum ether); $[\alpha]^{19}{}_D = -47.44$ (C=0.0113, CHCl$_3$); IR (neat) 3070 (W), 3050 (w), 3020 (W), 3000 (w), 2958 (s), 2930(s), 2895 (m), 2860 (s), 1742 (s), 1430 (s), 1255 (s), 1110 (s), 700 (s) cm$^{-1}$; $^1$H-NMR (500 MHz, CDCl$^3$) δ: 7.77-7.60 (m, 8H, aromatic), 7.45-7.33 (m, 12, aromatic), 6.19 (dd, 1H, J=11 Hz, 15.5 Hz, H-9), 5.91 (dd 1H, J=11 Hz, 15 Hz, H-10), 5.68 (dd, 1H, J=6.5 Hz, 15.5 Hz, H-11), 5.38-5.25 (m, 3H, H-8, H-14, H-15), 4.46-4.54 (m, 1H, H-5), 4.25-4.15 (m, 1H, H-12), 3.65 (s, 3H, COOCH$_3$), 2.29 (t, 2H, J=7Hz, H-2), 2.28-2.23 (m, 1H) and 2.23-2.13 (m, 1H, H-13), 2.07-1.94 (m, 2H, H-16) 1.9-1.68 (m, 6H, —CH$_2$—), 1.52-1.4 (m, 2H, —CH$_2$—), 1.35-1.25 (m, 2H, —CH$_2$—), 1.085 (s, 9H, $^t$Bu ), 1.075 (s, 9H, $^t$Bu), HRMS: Calc'd. for (M-1) $C_{53}H_{64}O_4F_3Si_2$; 877.429, found: 877.430 (FAB).

g. Preparation of:
Methyl-20,20,20-trifluoro-5(S), 12(R)-bis[[(1,1-dimethylethyl)diphenylsilyl]oxy]-6(Z), 8(E), 10(E), 14(Z)-eicosatetraenoate (Compound 18)

To a $^n$-hexane solution of 17 (91 mg, 0.103 mmol) in 10 ml of $^n$-hexane), 15 mg of Lindlar catalyst (Fluka, 16 wt %) was added and stirred for 15 hours under a hydrogen atmosphere (balloon). An additional 12 mg of catalyst (13 wt %) was added and stirred until 17 was consumed (9 hours) monitored by TLC (2% EtOAc-petroleum ether, developed twice). Catalyst was removed by filtration over celite, and the filtrate was concentrated under reduced pressure. Purification on TLC (0.5 mm thick, 2 plated, 2% EtOAc-petroleum ether, developed twice) provided 67 mg of 18 in 73.5% yield.

18: oil; Rf=0.258 (2% EtOAc-petroleum ether, 2 times development); $[\alpha]^{19}{}_D = +37.14$ (C=0.0091, CHCl$_3$), IR (neat) 3065 (w), 3045 (w), 3015 (w), 2995 (w), 2930 (s), 2890 (m), 2855 (s) 1740 (s), 1440 (s), 1255 (s), 1110 (s), 700 (s) cm$^{-1}$. $^1$H-NMR (250 MHz, CDCL$_3$) δ: 7.76-7.5 (m, 8H, aromatic), 6.0-5.52 (m, 5H, olefinic), 5.5-5.28 (m, 3H, olefinic), 4.56-4.44 (m, 1H, H-5), 4.23-4.15 (m, 1H, H-12), 3.61 (s, 3H, —COOCH$_3$), 2.35-2.12 (m, 4H, H-2, H-13), 2.12-1.75 (m, 4H, —CH$_2$—), 1.62-1.15 (m, 8H, —CH$_2$—), 1.08 (s, 9H, $^t$Bu), 1.04 (s, 9H, $^t$Bu). HRMS Calc'd. for $C_{53}H_{67}O_4F_3Si_2$: 880.453, found: 880.450.

h. Preparation of Methyl-20,20,20-trifluoro-LTB4 (Compound 19)

To a magnetically stirred solution of 18 (66.5 mg)m 0.075 mmol) in THF (2.5 ml) at room temperature was added $^n$Bu$_4$NF (1M THF solution, 0.5 ml, 0.5 mmol) under an argon atmosphere. The reaction mixture was stirred for 4.5 hours (TLC monitoring) and diluted with either (50 ml) and H5 buffer (20 ml). The aqueous layer was extracted with ether until it showed no free acid spot on TLC. After drying over MgSO$_4$ and concentration under reduced pressure, the extracts were treated with CH$_2$N$_2$. Excess CH$_2$N$_2$ was babbled off with argon. Concentration and purification on silica gel plate (20% petroleum ether in ether) gave 19 (17 mg) in 55.8% yield. 19; oil: Rf=0.128 (30% petroleum in ether) $[\alpha]^{22}{}_D+17.89$ (C=0.00833 (g/ml), CHCl$_3$)

UV: in CH$_3$OH, $1.88 \times 10^{-5}$ M
max 260 mm (ε:30000)
270 mm (ε:40000)
281 mm (ε:32000)

IR (neat): 3600 (broad, s), 3020 (m), 2945 (s), 2860 (m) 1740 (s), 1255 (s), 1135 (s), 1030 (s), 995 (s) cm$^{-1}$; NMR (500 MHz, CDCl$_3$) δ: 6.47 (dd, J=11.6 Hz, 14.2 Hz, 1H, H-8), 6.31-6.16 (m, 2H, H-9, H-10), 6.06 (dd, J=11 Hz, 11.6 Hz, 1H, H-7), 5.74 (dd, 1H, J=6.4 Hz, 14,7 Hz, H-11), 5.55-5.50 (m, 1H, H-6), 5.50-5.37 (m, 2H, H-14, 15), 4.57 (dt, J=8.4 Hz, 7 Hz, 1H, H-5), 4.02 (dt, J=6.4 Hz, 6.4 Hz, 1H, H-12), 3.65 (s, 3H, —CH$_3$), 2.36-2.26 (m, 4H), 2.09-1.98 (m, 9H), 1.75-1.47 (m, 10H, —CH$_2$—OH), HRMS. (CI) Calc'd. for $(M-OH)^+$: $C_{21}H_{29}O_3F_3$: 386.207, found: 386.205.

i. Preparation of : 20,20,20-Trifluoro-LTB4

To the magnetically stirred solution of 19 (5 mg, 0.012 mmol) in 0.15 ml of a mixture of THF-MeOH-H$_2$) (4:1:1) at 0° C., solid Lithium hydroxide monohydrate (2.6 mg, 5 eq) was added. After 1.5 hours, the reaction mixture was poured into a mixture of ether (30 ml) and pH5 buffer (5 ml), and the aqueous layer was extracted with ether (15 ml) twice. The combined organic layers were dried over MgSO$_4$ and concentrated under reduced pressures. Purification on silica gel plate (0.5 mm thick, ¼ plate, 8% CH$_3$OH in ether) provided 3 mg of the title compound (62.2%).

oil; Rf=0.149 (2% CH$_3$OH in ether); $[\alpha]^{20}{}_D = +17.33$ (C=0.0045, CHCl$_3$); UV (in CH$_3$OH, $2.3 \times 10^{-5}$ M) max=281 nm (ε25000), 270 nm (ε32000), 261 nm (ε24000) IR (CHCl$_3$ soln.) 3605 (w), 3005 (s), 2940 (s), 2860 (m), 1710 (s), 1255 (s), 1135 (s), 995 (s), 970 (w) cm$^{-1}$; $^1$H-NMR (500 MHz, CDCl$_3$) α: 6.474 (dd, 1H, J=11.8 Hz, 14.3 Hz), 6.32 6.18 (m, 2H), 6.068 (dd, 1H, J=11.1 Hz), 5.758 (dd, 1H, J=6.3 Hz, 14.9 Hz, H-11), 5.54 5.51 (m, 1H, H-6), 5.48-5.35 (m, 2H, 14-H, H-15), 4.65-4.55 (m, 1H, H-5), 4.25-4.15 (m, 1H, H-12), 2.45-2.2 (m, 4H), 2.15-1.9 (m, 4H), 1.8-1.62 (m. 3H), 1.62-1.48 (m, 3H), 1.48-1.35 (m, 2H); HRMS. Calc'd. for (M+1): $C_{20}H_{30}O_4F_3$: 391.210, found: 391.207.

Tests indicate that 20,20,20-trifluoro LTB4 is a partial agonist of LTB4 for chemotaxis but an antagonist for degranulation.
What is claimed is:
1. The compound of the formula
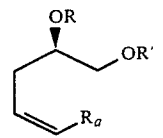
where R is Si(t-Bu)(phenyl)$_2$, R' is tetrahydropyran, and R$_a$ is —(CH$_2$)$_4$—CF$_3$.
* * * * *

UNITED STATES PATENT AND TRADEMARK OFFICE
CERTIFICATE OF CORRECTION

PATENT NO. : 5,110,949

DATED : May 5, 1992

INVENTOR(S) : Abe et al.

Page 1 of 4

It is certified that error appears in the above-identified patent and that said Letters Patent is hereby corrected as shown below:

On the title page, item [56] References Cited:
Column 1, Line 26, delete "Nicolaon" and insert therefor --Nicolaou--.

Column 2, line 2, delete "Nicolaon" and insert therefor --Nicolaou--.

Column 1, line 32, delete "LBT4" and insert therefor --LTB4--.

Column 1, line 43, delete "North.," and insert therefor --North,--.

Column 1, line 44, please insert--(-- before "1983).".

Column 3, line 10 delete "know" and insert therefor --known--.

Column 3, line 61 delete "this for" and insert therefor --this invention for--.

Column 6, line 7 delete "the" and insert therefor --The--.

Column 6 line 47 delete "1890," and insert therefor --1890--.

Column 6, line 54 delete "'Bu," and insert therefor --'Bu),--.

Column 8, line 18 delete "(W)" and insert therefor --(w)--.

Column 8, line 22 delete "10,6" and insert therefor --10.6--.

Column 8, line 24 delete "H8" and insert therefor --H-8--.

UNITED STATES PATENT AND TRADEMARK OFFICE
CERTIFICATE OF CORRECTION

PATENT NO. : 5,110,949

DATED : May 5, 1992

INVENTOR(S) : Abe et al.

It is certified that error appears in the above-identified patent and that said Letters Patent is hereby corrected as shown below:

Column 8, line 24 delete "14,15" and insert therefor --14.15--.

Column 8, line 26 delete "1.35-1.14," and insert therefor --1.35-1.14--

Column 8, line 47 delete "15/1," and insert therefor --15.1,--.

Column 8, line 51 delete "$^t$Bu," and insert therefor --$^t$Bu),--.

Column 8, line 67 insert --(-- before "gradient"

Column 9, line 10 delete "423" and insert therefor --4.23--.

Column 9, line 22 delete "15 ml)" and insert therefor --(15 ml)--.

Column 9 line 36 delete "(1.18)" and insert therefor --(1.18g)--.

Column 9, line 54 delete "wa" and insert therefor --was--.

Column 10, line 7 delete "oxy1" and insert therefor --oxy]--.

Column 10, line 40 delete "com-" and insert therefor --Com- --.

Column 10, line 50 insert --)-- after "aromatic"

Column 11, line 24 delete "o.233" and insert therefor --0.233--.

UNITED STATES PATENT AND TRADEMARK OFFICE
CERTIFICATE OF CORRECTION

PATENT NO. : 5,110,949

DATED : May 5, 1992

INVENTOR(S) : Abe et al.

Page 3 of 4

It is certified that error appears in the above-identified patent and that said Letters Patent is hereby corrected as shown below:

Column 11, line 39 delete "CDCl$^3$" and insert therefor --CDCl$_3$--.

Column 11, line 46 after (m, 2H, H-16) insert --,--.

Column 12, line 2 after (s) insert --,--.

Column 12, line 4 delete "CDCL$_3$" and insert therefor --CDCl$_3$--.

Column 12 line 18 delete "H5" and insert therefor --pH5--.

Column 12, line 35 delete "6.16" and insert therefor --6.17--.

Column 12, line 36 delete "14,7" and insert therefor --14.7--.

Column 12, line 61 delete "α" and insert therefor --δ--.

Column 12, line 62 insert -- - -- between "6.32 6.18".

Column 12, line 63 insert --,11.1 Hz)-- after "J=11.1 Hz".
Column 12, line 64 insert -- - -- between "5.54 5.51".
Column 12 line 66 delete "(m. 3H)" and insert therefor --(m, 3H)--.

UNITED STATES PATENT AND TRADEMARK OFFICE
CERTIFICATE OF CORRECTION

PATENT NO. : 5,110,949
DATED : May 5, 1992
INVENTOR(S) : Abe et al.

It is certified that error appears in the above-indentified patent and that said Letters Patent is hereby corrected as shown below:

Column 12, line 66, delete "(m. 3H)" and insert --(m, 3H)--.

Signed and Sealed this

Twenty-eighth Day of September, 1993

Attest:

BRUCE LEHMAN

Attesting Officer     Commissioner of Patents and Trademarks